United States Patent [19]

Cruickshank

[11] Patent Number: 5,082,935
[45] Date of Patent: Jan. 21, 1992

[54] DIAGNOSTIC REAGENTS MADE BY ATTACHING CYTIDINE CONTAINING NUCLEIC ACID PROBES TO AMINO FUNCTIONALIZED SOLID SUPPORTS BY BISULFITE MEDIATED TRANSAMINATION

[75] Inventor: Kenneth A. Cruickshank, Naperville, Ill.

[73] Assignee: Amoco Corporation, Chicago, Ill.

[21] Appl. No.: 284,545

[22] Filed: Dec. 15, 1988

[51] Int. Cl.$^5$ ............................................. C07H 21/00
[52] U.S. Cl. .............................. 536/27; 435/6; 435/808; 436/501; 536/26; 536/28; 935/25; 935/78
[58] Field of Search .................... 435/6, 808; 436/501; 536/26, 27, 28; 935/25, 78

[56] References Cited

U.S. PATENT DOCUMENTS

| | | | |
|---|---|---|---|
| 4,139,346 | 2/1979 | Rabbani | 422/56 |
| 4,358,535 | 11/1982 | Falkow et al. | 435/5 |
| 4,626,501 | 12/1986 | Landes | 435/6 |
| 4,689,295 | 8/1987 | Taber et al. | 435/6 |

FOREIGN PATENT DOCUMENTS

| | | |
|---|---|---|
| 0191640 | 8/1986 | European Pat. Off. |
| 0251527 | 1/1988 | European Pat. Off. |
| 0259186 | 3/1988 | European Pat. Off. |
| 86/01280 | 2/1986 | PCT Int'l Appl. |
| 2169403 | 7/1986 | United Kingdom |

OTHER PUBLICATIONS

Southern, E., J. Mol. Biol., 98, 503 (1975).
Smith, et al., Ann. Clin. Biochem., 18:253–274 (1981).
Prog. Nucl. Acid Res. Mol. Biol., 16:75 (1976), "Bisulfite Modification of Nucleic Acids and Their Constituents", Hikoya Hayatsu.
Draper, D. E., Nucleic Acid Research, vol. 12, No. 2, 1984, p. 989.
Reisfeld et al., Biochemical and Biophysical Research Communications, vol. 142, No. 2, 1987, Jan. 30, 1987, p. 519.
Gillam et al., Analytical Biochemistry, 157, 199–207 (1986) pp. 199.
Sono et al., Journal of the American Chemical Society, 95, 14, Jul. 14, 1973, p. 4746.
Schulman et al., Nucleic Acids Research, vol. 9, Nov. 5, 1981, p. 1203.
Summerton, J. Theor. Biol. (1979) 78, 61–75.
Kornberg, DNA Replication, W. H. Freeman and Co., San Francisco, 1980, pp. 670–679.
So et al., Infect. Immun., 21:405–411, 1978.
M. Caruthers, Genetic Engineering, pp. 119–145, Plenum Press, New York and London (1982).

Primary Examiner—Robert A. Wax
Assistant Examiner—Ardin H. Marschel
Attorney, Agent, or Firm—Norval B. Galloway; William H. Magidson; Ralph C. Medhurst

[57] ABSTRACT

This invention encompasses diagnostic reagents comprising a polynucleic acid probe having a specific binding sequence and having one or more cytidines outside of the specific binding sequence. The polynucleic acid probe is bound to an amino functionalized solid support by a bisulfite mediated transamination between a cytidine and an amino group on the solid support. When the specific binding sequence contains cytidine, the cytidine is replaced with 5-methylcytidine which has essentially the same binding capacity and yet does not participate in transamination reactions. The invention encompasses compositions of the polynucleic acid probe as well as test kits including the above identified reagent and assays utilizing the above reagent. This invention is useful in detecting viruses, fungi and bacteria in test samples such as body fluids and food samples as well as detecting DNA or RNA sequences in mammalian cells.

16 Claims, 1 Drawing Sheet

DIAGNOSTIC REAGENTS MADE BY ATTACHING CYTIDINE CONTAINING NUCLEIC ACID PROBES TO AMINO FUNCTIONALIZED SOLID SUPPORTS BY BISULFITE MEDIATED TRANSAMINATION

BACKGROUND OF THE INVENTION

This invention is in the field of diagnostic reagents and methods for detecting deoxyribonucleic (DNA) or ribonucleic acid (RNA) sequences in test samples. The invention relates to the field of binding DNA to a solid support.

The present invention encompasses methods, reagents, compositions, and kits for detecting deoxyribonucleic acid (DNA) or ribonucleic acid (RNA) from test samples. Embodiments of the present invention provide methods for rapid, sensitive detection of nucleic acid targets in food or clinical samples such as body fluids which contain viruses, or bacteria. These reagents and methods are adaptable to non-radioactive labeling techniques and automation and are equally applicable to other DNA and RNA containing cells such as mammalian cells and fungi.

The term "polynucleic acid probe" refers to a nucleic acid sequence having a specific binding sequence or region and one or more cytidines generally a polycytidine region wherein cytidines in the specific binding sequence are replaced with 5-methylcytidine. The specific binding sequence may be directly bindable to the nucleic acid sequence to be determined or it may be bindable to a nucleic acid sequence bound to the sequence to be determined. The specific binding sequence may be complementary to nucleic acid sequences of variable nucleic acid residues or it may be complementary to homopolymer segments such as polyadenosine, polyguanosine, polythymidine, or poly-5-methylcytidine. The polycytidine region of the polynucleic acid probe may be at the end of the probe or it may be centrally located with nucleic acid sequences on either side, for example, a polycytidine region with two specific binding sequences on either side.

The term "label" refers to a molecular moiety capable of detection including, by way of example, without limitation radioactive isotopes, enzymes, luminescent agents and dyes The term "agent" is used in a broad sense, including any molecular moiety which participates in reactions which lead to a detectable response Also biological detecting systems may be employed e.g., bacteriophage oligonucleotide conjugates.

The term "retrievable" is used in a broad sense to describe an entity which can be substantially dispersed within a medium and removed or separated from the medium by immobilization, filtering, partitioning, or the like.

The term "support" when used includes conventional supports such as nitrocellulose or nylon filters, membranes, beads, and dip sticks and microtiter plate wells, as well as retrievable magnetic supports. A solid support is a separation medium by which nucleic acid sequences can be selectively bound and then separated from other components of the reaction mixture.

Genetic information is contained in living cells in threadlike molecules of DNA. In vivo, the DNA molecule is a double helix each strand of which is a chain of nucleotides. Each nucleotide is characterized by one of four bases: adenine (A), guanine (G), thymine (T). and cytosine (C). The bases are complementary in the sense that, due to the orientation of functional groups, certain base pairs attract and bond to each other through hydrogen bonding. Adenine in one strand of DNA pairs with thymine in an opposing complementary strand. Guanine in one strand of DNA pairs with cytosine in an opposing complementary strand. In RNA, the thymine base is replaced by uracil (U) which pairs with adenine in an opposing complementary strand.

DNA consists of covalently linked chains of deoxyribonucleotides and RNA consists of covalently linked chains of ribonucleotides. The genetic code of a living organism is carried upon the DNA strand in the sequence of the base pairs.

Each nucleic acid is linked by a phosphodiester bridge between the five prime hydroxyl group of the sugar of one nucleotide and the three prime hydroxyl group of the sugar of an adjacent nucleotide. Each linear strand of naturally occurring DNA or RNA has one terminal end having a 5'-hydroxyl group and another terminal end having a 3'-hydroxyl group. The terminal ends of polynucleotides are often referred to as being 5'-terminal or 3'-terminal in reference to the respective free hydroxyl group. Complementary strands of DNA and RNA form antiparallel complexes in which the 3'-terminal end of one strand is oriented and bound to the 5'-terminal end of the opposing strand.

Nucleic acid hybridization assays are based on the tendency of two nucleic acid strands to pair at complementary regions. Presently, nucleic acid hybridization assays are primarily used to detect and identify unique DNA or RNA base sequences or specific genes in a complete DNA molecule, in mixtures of nucleic acid, or in mixtures of nucleic acid fragments.

The identification of unique DNA or RNA sequences or specific genes within the total DNA or RNA extracted from tissue or culture samples may indicate the presence of physiological or pathological conditions. In particular, the identification of unique DNA or RNA sequences or specific genes, within the total DNA or RNA extracted from human or animal tissue, may indicate the presence of genetic diseases or conditions such as sickle cell anemia, tissue compatibility cancer and precancerous states, or bacterial or viral infections The identification of unique DNA or RNA sequences or specific genes within the total DNA or RNA extracted from bacterial cultures or tissue containing bacteria may indicate the presence of antibiotic resistance, toxins, viruses, or plasmids, or provide identification between types of bacteria.

Thus, nucleic acid hybridization assays have great potential in the diagnosis and detection of disease Further potential exists in agriculture and food processing where nucleic acid hybridization assays may be used to detect plant pathogenesis or toxin-producing bacteria.

One of the most widely used nucleic acid hybridization assay procedures is known as the Southern blot filter hybridization method or simply, the Southern procedure (Southern, E., *J. Mol. Biol. I.,* 98, 503, (1975)). The Southern procedure is used to identify target DNA or RNA sequences. This procedure is generally carried out by immobilizing sample RNA or DNA to nitrocellulose sheets as the solid support. The immobilized sample RNA or DNA is contacted with radio-labeled probe strands of DNA having a base sequence complementary to the target sequence carrying a radioactive moiety which can be detected. Hybridization between the probe and the sample DNA is allowed to take place.

The hybridization process is generally very specific. The labeled probe will not combine with sample DNA or RNA if the two nucleotide entities do not share substantial complementary base pair organization. Hybridization can take from three to 48 hours depending on given conditions.

However, as a practical matter there is always nonspecific binding of the labeled probe to supports which appears as "background noise" on detection. Background noise reduces the sensitivity of an assay. Unhybridized DNA probe is subsequently washed away. The nitrocellulose sheet is placed on a sheet of X-ray film and allowed to expose. The X-ray film is developed with the exposed areas of the film identifying DNA fragments which have been hybridized to the DNA probe and therefore have the base pair sequence of interest.

The use of radioactive labeling agents in conjunction with Southern assay techniques have allowed the application of nucleic acid assays to clinical samples. Radioactive decay is detectable even in clinical samples containing extraneous proteinaceous and organic material. However, the presence of extraneous proteinaceous and organic material may contribute to nonspecific binding of the probe to the solid support. Moreover, the use of radioactive labeling techniques requires a long exposure time to visualize bands on X-ray film A typical Southern procedure may require 1 to 7 days for exposure. The use of radioactive labeling agents further requires special laboratory procedures and licenses.

The above problems associated with assays involving radioisotopic labels have led to the development of techniques employing nonisotopic labels. Examples of nonisotopic labels include enzymes, luminescent agents, dyes and biological detecting systems such as bacteriophage. Luminescent labels emit light upon excitation by an external energy source and may be grouped into categories dependent upon the source of the exciting energy, including: radioluminescent labels deriving energy from high energy particles; chemiluminescent labels which obtain energy from chemical reactions; bioluminescent labels wherein the exciting energy is applied in a biological system; and photoluminescent or fluorescent labels which are excitable by units of electromagnetic radiation (photons) of infrared, visual or ultraviolet light See, generally, Smith et al., *Ann. Clin. Biochem.*, 18:253, 274 (1981).

Nonisotopic assay techniques employing labels excitable by nonradioactive energy sources avoid the health hazards and licensing problems encountered with radioisotopic label assay techniques. Moreover, nonisotopic assay techniques hold promise for rapid detection avoiding the long exposure time associated with the use of X-ray film.

However, nonisotopic assays have not conveyed the sensitivity or specificity to assay procedures necessary to be considered reliable. In luminescent assays, the presence of proteins and other molecules carried in biological samples may cause scattering of the exciting light or may absorb light in the spectrum of emission of the luminescent label, resulting in a quenching of the luminescent probe.

In enzymatic assays, the presence of proteins and other molecules carried in biological samples may interfere with the activity of the enzyme.

Similarly, in colorimetric assays, the change in color may not be detectable over proteins and other materials carried in biological samples.

The use of polynucleic acid probes in diagnostic assays for DNA and RNA is extensively taught in the prior art.

U.S. Pat. No. 4,358,535 extensively discusses the detection of various pathogens using labeled polynucleotide probes. Thus probes, hybridization conditions and methods for detecting labeled probes are well known.

U.S. Pat. No. 4,689,295 describes a test for salmonella using probes specific for salmonella DNA This patent describes in detail the culturing, lysing, and sample preparation techniques. This patent also describes fixing DNA to nitrocellulose filters.

U.S. Pat. No. 4,626,501, EPA 259,186 and EPA 251,527 describe DNA probe assays on solid supports.

PCT/US 86/01280 application describes various configurations of nucleic acid hybridization assays widely applicable to detecting nucleic acid sequences specific to various bacteria and viruses.

U.S. Pat. No. 4,139,346 describes nucleic acid probes covalently bound to a support paper modified with aminobenzyloxymethyl groups.

U.K. Patent Application GB 2169403A describes the formation of a complex where the DNA or RNA to be detected is bound to two probes in different complementary regions. One probe is labeled with a detectable marker and the other probe is bindable on a support so that it can be captured by a membrane having a binding partner.

The prior art also describes bisulfite catalyzed transamination reactions with cytidine.

Of the four nucleic acids, cytidine uniquely undergoes transamination reaction in the presence of bisulfite.

Bisulfite modifications of nucleic acids is extensively discussed in *Prog. Nucl. Acid Res. Mol. Biol.*, 16: 75 (1976). "Bisulfite Modification of Nucleic Acids and their Constituents," (Hikoya Hayatsu).

*Nucleic Acid Research*, Volume 12, Number 2, 1984, pg. 989, describes the attachment of reporter groups to specific, selected cytidine residues in RNA using a bisulfite catalyzed transamination reaction.

*Biochemical and Biophysical Research Communications*, Vol 142, No. 2, 1987, Jan. 30, 1987, pp. 519, describes the linking of cytidine to a biotin hydrazide using a bisulfite catalyzed reaction.

*Analytical Biochemistry*, 157, 199-207 (1986), pp 199, describes $N^4$(6-aminohexyl)cytidine and cytidine-containing nucleotides where these compounds are formed using a bisulfite catalyzed transamination reactions.

*Journal of the American Chemical Society*, 95, 14, July 14, 1973, pp. 4746, describes bisulfite catalyzed isotope exchange on cytidine.

*Nucleic Acids Research*, Vol. 9, Nov. 5, 1981, pp. 1203 coupling t-RNA with N-hydroxysuccinimide by way of a bisulfite catalyzed transamination.

*J. Chem. Biol.*, 1979, 78(i), 61-75 describes the bisulfite catalyzed transamination of cytidine and acylhydrazides.

SUMMARY OF THE INVENTION

Figure 1:
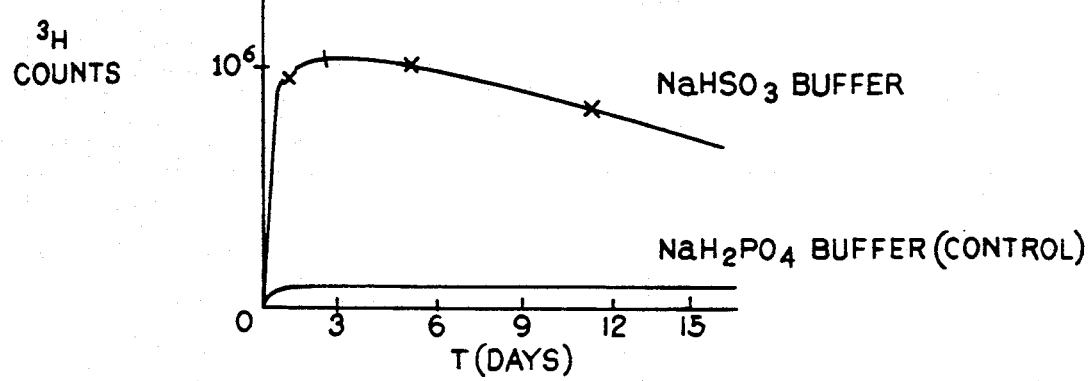
FIG. 1 illustrates attachment of DNA to a solid support by a transamination reaction.

This invention encompasses diagnostic reagents comprising a polynucleic acid probe having a specific binding sequence and having a region of one or more cytidines, generally a polycytidine, wherein any cytidines in the specific binding sequence are replaced with 5-methylcytidine and wherein the polynucleic acid probe is bound to an aminofunctionalized solid support by a bisulfite mediated transamination reaction between the cytidine and the amino group of the solid support.

The cytidines provide for site specific binding of the polynucleic acid probe to the solid support. The cytidine region may be located at the 3' or 5' end of the specific binding sequence or the cytidine region may be an internal sequence having nucleic acid sequences on either side where at least one of the side sequences preferably both are specific binding sequences. Any cytidines in the specific binding sequence are replaced with 5-methylcytidine The 5-methylcytidine does not interfere with the specific binding but prevents bisulfite catalyzed transamination reaction. This feature of the invention permits site specific binding of the cytidine region of the probe to the solid support.

The specific binding sequence of the polynucleic acid probe may be complementary and directly bindable to the DNA or RNA sequence to be detected or the specific binding sequence may be complementary to a portion of a nucleic acid sequence which is bound to the nucleic acid sequence to be determined. The specific binding sequence also includes homopolymer sequences such as polyadenosine, polyguanosine, polythymidine and poly 5-methylcytidine.

The reagents of this invention are useful in a variety of test configurations for detecting genetic material from cells including mammalian cells, viruses, bacteria, and fungi.

DETAILED DESCRIPTION OF THE INVENTION

The polynucleotide probes are made by conventional automated methods for synthesizing polynucleic acids M. Caruthers, *Genetic Engineering, pp.* 119-145, Plenum Press, New York and London (1982). These methods involve the repetitive formation of an ester linkage between an activated phosphoric acid function of one nucleotide and the hydroxyl group of another nucleotide forming a phosphodiester bridge The exception is that the cytidines in the specific binding sequence are replaced with 5-methylcytidine. In one embodiment the polynucleic acid probe terminates at the 3' or 5' end with 1 to 100 cytidines, preferably 1 to 10 cytidines. In another embodiment the cytidine region has nucleic acid sequences on both ends at least one of which is a specific binding sequence. In this embodiment the polycytidine region is about 5 to 10 cytidines. These probes are suitable for binding to an amino functionalized support by a bisulfite catalyzed transamination reaction.

The amino functionalized solid supports are well known. Amino functionalized magnetic beads of iron oxide coated with organic polymers containing an amino group are sold by Advanced Magnetics, Inc . 61 Moony Street. Cambridge, Mass. 02138. Polystyrene microspheres with amino groups are sold by Polysciences, Inc., 400 Valley Road, Warrington, Pa. 18976.

Polystyrene supports can be conveniently functionalized by the acid catalyzed reaction of the polystyrene with N-hydroxymethylphthalimide followed by treatment with hydrazine to provide an aminomethyl group on the phenyl ring as illustrated in more detail in Example 1.

The polynucleic acid probe is bound to the amino functionalized support by reaction in about 2 0 molar bisulfite solution typically.

The support may be in the form of titer plate wells, dip sticks, beads, filter membranes and the like. The only requirement is the availability of free amino groups for the bisulfite catalyzed transamination. The amino groups can be on a polymer which is then coated on the solid support so that the amino groups are available for a transamination reaction.

Scheme I illustrates binding nucleic acids to an amino functionalized support as follows:

Scheme I

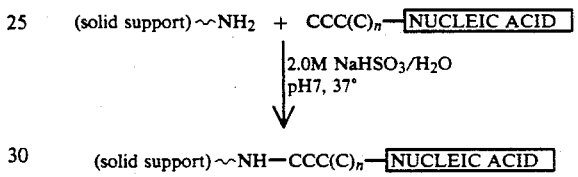

Cytidines in the nucleic acid moiety are replaced with 5-methylcytidine.

Scheme II illustrates a target capture of poly G by a poly 5-methylcytidine probe.

Scheme II

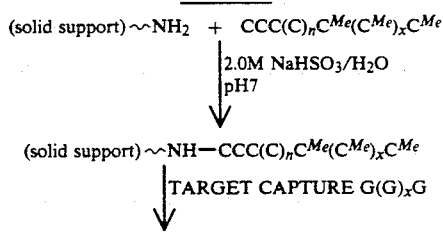

Scheme III

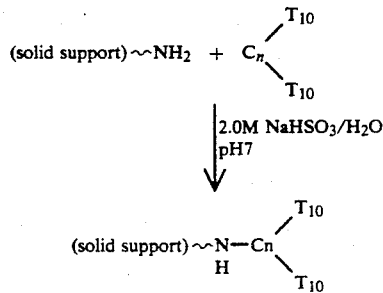

Scheme III illustrates non-terminal cytidines reacting to produce "branched" 60 nucleic acid structures on the solid support.

In Schemes I and II n is equal to or greater than zero but generally is a number that provides for 1 to 100 cytidines preferably 1 to 10. In Scheme III n is generally between 5 and 10.

Figure 2A:
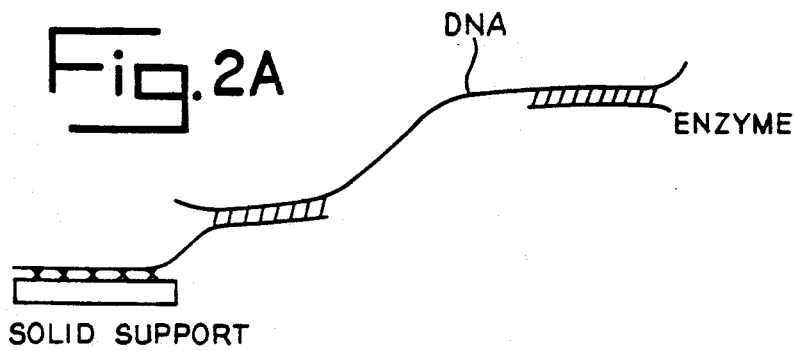
FIG. 2A illustrates a specific binding sequence complementary to the DNA to be determined.
Figure 2B:
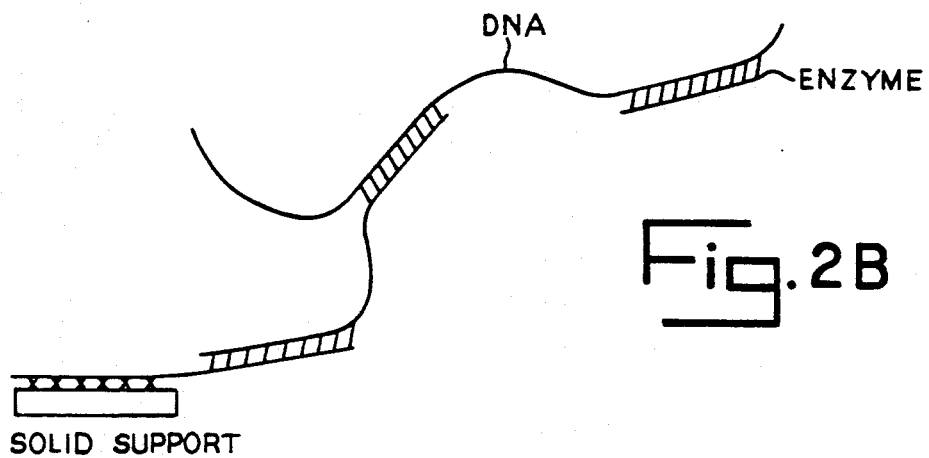
FIG. 2B illustrates a specific binding sequence complementary to a section of polynucleic acid which is not complementary to the DNA to be determined.

The specific binding sequence may be complementary to a segment of the DNA or RNA to be determined as illustrated in FIG. 2A or the specific binding sequence may be complementary to a segment of a polynucleic acid where the polynucleic acid has another segment complementary to the DNA or RNA to be determined as illustrated by FIG. 2B.

The labeled probe may be obtained from messenger RNA. from cDNA obtained by reverse transcription of messenger RNA with reverse transcriptase or by cleavage of the genome, conveniently by endonuclease digestion, followed by cloning of the gene or gene fragment in accordance with known techniques. See, for example, Kornberg, *DNA Replication*, W. H. Freeman and Co., San Francisco, 1980, pp. 670-679;Dallas et al. supra; So et al., supra; So et al. *Infect. Immun.* 21:405-411, 1978. After isolation and characterization of the desired gene or DNA fragment, the gene or DNA fragment may be used for preparation of the labeled probe or cloned for production of messenger RNA, which may then be used for preparation of the probe.

Enzymes of interest as labels will primarily be hydrolases, particularly esterases and glycosidases, or oxidoreductases, particularly peroxidases. Fluorescent compounds include fluorescein and its derivatives, rhodamine and its derivatives, dansyl, umbelliferone, etc. Chemiluminescers include luciferin, and 2,3-dihydrophthalazinediones, e.g. luminol Viral detection agents include bacteriophage, X 174 and M 13.

The oligomer 3'-TTT TTT TTT TCC CCC-5 was prepared on a DNA synthesizer by the phosphoramidite method. The oligomer was then radioactively labeled by the enzymatic addition of several $^3$H-TTP residues using terminal deoxynucleotidyl transferase A fine dispersion of the amino functionalized latex beads in aqueous 1M sodium bisulfite solution at pH 7 was formed by sonication and the $^3$H-DNA was then added. At intervals, aliquots of the bead suspension were removed, the beads isolated and the amount of DNA bound to the support was determined by scintillation counting. The results are displayed graphically in FIG. 1. These results illustrate that the DNA oligomer has been attached to the support.

Table I further illustrates the time binding of DNA to the support.

TABLE I

TIME-COURSE OF $C_5T_{10}$ BINDING TO BENZYLAMINE SUPPORT

| Days | $^{32}$P(dN)$_{50}$ | IA HSO$_3$ [C$_5$T$_{10}$] = 10 D/ml | IIA HSO$_3$ [C$_5$T$_{10}$] = 20 D/ml | IB Control (Phosphate) |
|---|---|---|---|---|
| | | dN$_{50}$ Capacity (ng/mg) | | |
| 1 | A | 30.91 | 23.38 | 15.25 |
| | T | 0.97 | 0.11 | 0.10 |
| | A | <0.48> | <0.23> | <0.37> |
| 3 | A | 171.18 | 169.93 | 11.70 |
| | T | 0.31 | 0.70 | 0.11 |
| | A | <6.77> | <2.91> | <0.01> |
| 5 | A | 167.37 | 204.25 | 7.40 |
| | T | 1.17 | 0.12 | 0.25 |
| | A | <12.78> | <5.19> | <0.17> |
| 12 | A | 231.97 | 182.99 | 21.82 |
| | T | 0.30 | 0.55 | 1.10 |
| | A | <16.50> | <10.27> | <0.14> |
| 20 | A | 180.08 | 263.01 | 8.12 |
| | T | 0.13 | 0.08 | 0.24 |
| | A | <17.76> | <20.33> | <0.80> |

Numbers in < > indicate signal counts left on beads after elution step.

Microorganisms which may be diagnosed include bacteria viruses, fungi, protozoa, molds etc Among toxin producing microorganisms are bacteria, such as gram negative bacilli e.g. Escherichia, Vibrio, Yersinia, Klebsiella and Salmonella Species include *E coli, Vibrio cholerae, Haemophilus ducrei*, Legionaire's bacillus. Other microorganisms of interest are those difficult to cultivate such as *Chlamydia trachomatis*. genital Herpes virus, HIV, Norwalk Agent, Rotavirus, Cytomegalovirus, *Campylobacter jejuni*.

Genetic material of mammalian cells such as oncogenes can likewise be detected.

The cells are treated to liberate their DNA (and/or RNA). If the cells are provided with nutrients to expand their numbers, after a sufficient time for the colonies to form, the filter is removed from the nutrient source and the cells lysed. Lysis conditions are devised such that the cells or colonies do not migrate and their DNA remains affixed in place on the surface where they were situated. The lysing and DNA denaturing as well as the subsequent washings can be achieved by placing the filter containing the cells or colonies, isolate side up, onto a bibulous support saturated with an appropriate solution for a sufficient time to lyse the cells and denature the DNA. For lysing, chemical lysing will conveniently be employed, usually dilute aqueous alkali e g. 0.1 to 1 M NaOH. The alkali will also serve to denature the DNA. Other denaturation agents include, elevated temperatures, organic reagents, e.g. alcohols, amides, amines, ureas, phenols and sulfoxides or certain inorganic ions, e.g. thiocyanate and perchlorate.

Denatured DNA can be transferred to an amino functionalized filter paper having a polynucleic acid probe bound to it. The filter paper is washed and reacted with a label probe having a complementary sequence to a different area of the DNA or RNA to be detected. The preparation of samples for detecting salmonella are described in detail in U.S. Pat. No. 4.689.295 which is incorporated herein by reference.

A procedure for testing for bacteria in food involves culturing about 25 grams of food in nutrient broth for about 24 hours at 30.37° C. A 1 ml aliquot of the culture is filtered so that bacteria will be collected on the filter. The bacteria are then lysed and denatured with a NaOH/NaCl solution and the lysate is removed from the filter and neutralized with tris buffer The lysate is then incubated with a reagent of this invention, i.e. support with a polynucleic acid probe specific to the bacteria being tested. The reagent (support) is then separated and washed with tris buffer to remove non-specifically bound material. The reagent is then reacted with a labeled probe which specifically binds to a different region of the DNA being tested and washed The label on the support is then measured.

The invention is illustrated further by the following examples which are not to be construed as limiting the invention in scope or spirit to the specific procedures described in them.

EXAMPLE 1

Amino Functionalization of Phenyl Groups of Solid Support

To 10 g divinylbenzene polystyrene beads was added in sequence, 75 ml dichloromethane, 75 ml trifluoroacetic acid, 15 g N-hydroxymethylphthalimide and finally 10 g trifluoromethylsulfonic acid. The resulting mixture was stirred at room temperature for sixteen hours and the beads were removed by filtration. The beads were then washed extensively with ethanol (1000 ml) water (1000 ml) and finally ethanol until the filtrate was neutral to pH paper. The beads were then treated with a solution of 8ml hydrazine monohydrate and 32ml water in 160ml ethanol and the resulting mixture was mechanically stirred at room temperature overnight. The beads were removed by filtration and washed extensively with ethanol (1000 ml), water (1000 ml) and finally ethanol until the washings no longer gave a coloration with picryl sulfonic acid (to ensure complete removal of the hydrazine). The beads were air dried and finally dried in vacuo at room temperature. This support was stored for use in the transmination chemistry. The above reactions are illustrated by the following scheme.

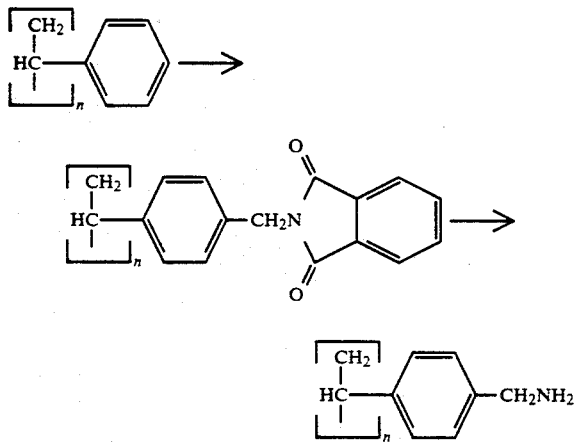

EXAMPLE 2

Hybridization of Nucleotide to Solid Support

A. Washing

A 2.5% (v/v) suspension of transaminated solid support in 20 mM sodium phosphate solution, pH7, was prepared. After centrifugation and decantation the solid support was washed 5 times with wash buffer 5X SSC. A stock of 20X SSC was prepared by adding 800ml of water to 175.3 g of sodium chloride 88.2g of sodium citrate, adjusting the pH to 7 with 1 M HCl and adding water to a final volume of 1l.

B. Prehybridization

A prehybridization buffer (PHB) was prepared from the following components. 3ml 10% (w/v) polyvinylpyrolidone, 3ml of 10% BSA 3ml of 10% (w/v) Ficoll 400 detergent, 2.2 ml salmon sperm DNA stock (10 mg/ml), 15 ml 20× SSC buffer stock and 250 mg yeast tRNA was dissolved in water to a final volume of 150ml A final wash was carried out at 55° C. in 500µl of PHB for 1 hour, followed by washing twice at room temperature with 5X SSC. The solid support was then prehybridized at room temperature for 3 hours with 500µl of PHB buffer and then again washed with wash buffer.

C. Hybridization

Hybridization was carried out in 500µl of PHB buffer to which had been added a radiolabelled polynucleotide, for example [$^{32}$P]dA$_{50}$ (50–100 µg/ml) at room temperature for 1 hour and then centrifuging at 200rpm on a rotator. After centrifugation and removal of the supernatent the solid support was then washed 5 times with PHB.

D. Thermal Elution Of The Bound Oligonucleotide

The solid support was incubated at 65° C. for 5 minutes in 500µl of 1X SSC. After centrifugation, the supernatent was removed and added to scintillation vials. This process was repeated and the supernatent was added to the original supernatent. E. The radioactivity in the supernatent and that still remaining on the solid support was determined by scintillation counting.

Table 2 illustrates the binding capacity of a polycytidine probe to various target nucleotides.

TABLE 2

| | Binding Capacity (ng/mg) $C(m^5C)_{10}C$-Support | | | |
|---|---|---|---|---|
| | Solid Support Before 65° C. Elution | | Solid Support After Elution | |
| $^{32}$P(dN)$_n$ | bisulfite | NaCl | bisulfite | NaCl |
| $^{32}$P-A$_{50}$ | 9.73 | 13.85 | 6.45 | 13.68 |
| $^{32}$P-T$_{50}$ | 2.33 | 2.38 | 1.33 | 1.18 |
| $^{32}$P-C$_{12-18}$ | 3.70 | 3.55 | 2.33 | 1.08 |
| $^{32}$P-G$_{12-18}$ | 152.50 | 26.48 | 151.90[1] | 22.35 |
| $^{32}$P-G$_{12-18}$ | 148.85 | 21.20 | 112.93[1] | 15.58 |
| $^{32}$P-t-RNA | 47.43 | 18.68 | 38.13 | 4.85 |

$^{32}$P-A$_{50}$ is phosphorous 32 labeled polyadenosine of about 50 residues.
$^{32}$P-T$_{50}$ is phosphorous 32 labeled polythymidine of about 50 residues.
$^{32}$P-C$_{12-18}$ is phosphorous 32 labeled polycytidine of 12 to 18 residues.
$^{32}$P-G$_{12-18}$ is phosphorous 32 labeled polyguanosine of 12 to 18 residues.
$^{32}$P-t-RNA is phosphorous 32 labeled t-RNA.
[1]These results indicate that the support in this case can irreversibly bind $^{32}$P-G$_{12-18}$.

EXAMPLE 3

Attachment of $T_{10}C_5T_{10}$ to Polystyrene Beads

Amino functionalized polystyrene beads (62 5mg) were suspended in 5ml of a pH 7, 2.5M NaHSO$_3$ solution Any clumps of beads were broken up first with a spatula and further with sonication for about fifteen minutes.

A $T_{10}C_5T_{10}$ probe solution having 5 OD's/ml (61) was added to the solution containing the polystyrene beads The mixture was placed on a rotator and circulated for three days at room temperature. A time course experiment indicated that maximum nucleic acid attachment occurred after three days of these conditions.

The reaction solution was washed four times with 20mM phosphate/25% ethanol incubating in 5ml buffer at 52 to 55° C. for one hour (to remove any non-specifically binding probe) and washing four additional times with buffer. After the final buffer wash, the beads were suspended in 2mL of buffer and stored in a refrigerator until used for hybridization.

Hybridization according to the procedures of Example 2 with A$_{50}$, T$_{50}$, and t-RNA are illustrated in the following Table 3.

TABLE 3

| | BINDING DATA | | |
|---|---|---|---|
| | | NUCLEIC ACID CAPACITY (ng/mg) | |
| Support | $^{32}$P-N,A. | NaCl | NaHSO$_3$— |
| PS-T$_{10}$C$_5$T$_{10}$ | A$_{50}$ | 17.18 | 265.80 |
| PS-T$_{10}$C$_5$T$_{10}$ | T$_{50}$ | 0.29 | 0.93 |
| PS-T$_{10}$C$_5$T$_{10}$ | t-RNA | 2.39 | 2.34 |

PS = polystyrene
The use of T$_{10}$C$_5$T$_{10}$ gives increased binding capacity of 35% relative to C$_5$T$_{10}$.

What is claimed is:

1. A diagnostic reagent comprising a polynucleic acid probe having a specific binding sequence and having a cytidine region of one or more cytidines outside of the specific binding sequence and wherein cytidines in the specific binding sequence are 5-methylcytidines, wherein the polynucleic acid probe is bound to an amino functionalized support by a bisulfite mediated transamination between a cytidine outside the specific binding sequence and an amino group on the support.

2. A diagnostic reagent according to claim 1 wherein the specific binding sequence is complementary to the DNA or RNA to be detected.

3. A diagnostic reagent according to claim 1 wherein the cytidine region is 1 to 100 cytidines at a terminal end of the polynucleic acid probe.

4. A diagnostic reagent according to claim 1 wherein the cytidine region is about 5 to 10 cytidines and is not at the terminal end of the polynucleic acid probe.

5. A diagnostic reagent according to claim 1 wherein the specific binding sequence is a homopolymer sequence selected from polyadenosine, polyguanosine, polythymidine, or poly 5-methylcytidine.

6. A diagnostic reagent according to claim 1 wherein the specific binding sequence binds to viral DNA or RNA.

7. A diagnostic reagent according to claim 1 wherein the specific biding sequence binds to bacterial DNA or RNA.

8. A diagnostic reagent according to claim 1 wherein the specific binding sequence binds to mammalian DNA or RNA.

9. A diagnostic reagent according to claim 1 wherein the specific binding sequence binds to fungal DNA or RNA.

10. A diagnostic test kit comprising:
    (a) a diagnostic reagent of claim 1 wherein the specific binding sequence is complementary to one portion of the DNA or RNA to be determined, or which is complementary to a portion of a polynucleotide bound to a DNA or RNA to be determined and
    (b) a labeled polynucleic acid probe having a specific binding sequence complementary to a second portion of the DNA or RNA to be determined.

11. A polynucleic acid probe comprising a specific binding sequence and containing outside of the specific binding sequence a cytidine region of one or more cytidines and wherein the cytidines in the specific binding sequence are 5-methylcytidines.

12. A polynucleic acid probe according to claim 11 wherein the specific binding sequence is complementary to the DNA to be determined.

13. A polynucleic acid probe according to claim 11 wherein the cytidine region is at a terminal end of the polynucleic acid probe.

14. A polynucleic acid probe according to claim 11 wherein the cytidine region is not at a terminal end of the polynucleic acid probe.

15. A polynucleic acid probe according to claim 11 wherein the specific binding sequence is a homopolymer sequence.

16. A method for detecting the presence of specific bacteria in bacteria containing samples comprising:
    (a) providing a sample suspected of containing the specific bacteria to be detected;
    (b) lysing the bacterial in said sample to release their DNA;
    (c) denaturing the DNA;
    (d) contacting the denatured DNA with a diagnostic reagent of claim 1 and allowing the DNA of the reagent to hybridize with the DNA of the bacteria to be detected;
    (e) washing the reagent to remove non-specifically bound material;
    (f) hybridizing a labeled probe to the bacteria DNA bound to the reagent;
    (g) washing the reagent to remove non-specifically bound DNA; and measuring the label on the reagent.

* * * * *